(12) United States Patent
Drezner et al.

(10) Patent No.: US 8,993,720 B2
(45) Date of Patent: Mar. 31, 2015

(54) METHODS FOR THE TREATMENT OF X-LINKED HYPOPHOSPHATEMIA AND RELATED DISORDERS

(75) Inventors: Marc K. Drezner, Madison, WI (US); Baozhi Yuan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 454 days.

(21) Appl. No.: 13/272,809

(22) Filed: Oct. 13, 2011

(65) Prior Publication Data

US 2012/0122790 A1    May 17, 2012

Related U.S. Application Data

(63) Continuation-in-part of application No. PCT/US2011/049776, filed on Aug. 30, 2011.

(60) Provisional application No. 61/393,132, filed on Oct. 14, 2010.

(51) Int. Cl.
| | | |
|---|---|---|
| C07K 11/00 | (2006.01) | |
| A61K 38/08 | (2006.01) | |
| A61K 38/10 | (2006.01) | |

(52) U.S. Cl.
CPC ................ *A61K 38/08* (2013.01); *A61K 38/10* (2013.01)
USPC ........... 530/329; 530/326; 530/327; 530/328; 530/330

(58) Field of Classification Search
USPC .......................... 530/329, 330, 326, 327, 328
See application file for complete search history.

(56) References Cited

U.S. PATENT DOCUMENTS

| | | | | |
|---|---|---|---|---|
| 2007/0099822 A1* | 5/2007 | Rowe | ................................ | 514/7 |
| 2009/0110677 A1* | 4/2009 | Yamashita et al. | ......... | 424/130.1 |
| 2009/0148461 A1* | 6/2009 | Yamazaki et al. | ......... | 424/152.1 |
| 2010/0249022 A1* | 9/2010 | Clapham et al. | ............... | 514/3.8 |

FOREIGN PATENT DOCUMENTS

| | | |
|---|---|---|
| WO | WO 95/29675 | 11/1995 |
| WO | WO 2008/067199 | 6/2008 |

OTHER PUBLICATIONS

Baum et al., Role of Prostaglandins in the Pathogenesis of X-Linked Hypophosphatemia: Pediatric Nephrology, 21:1067-1074 (2006).
Gaasbeek et al., Hypophosphatemia: An Update on its Etiology and Treatment, The American Journal of Medicine, 118:1094-1101 (2005).
International Search Report dated Dec. 23, 2011 for PCT Application No. PCT/US2011/049776.
Yuan et al., "The 7132 Protein Regulates FGF-23 Degradaton and Production in X-Linked Hypophosphatemia" Journal of Bone and Mineral Research, 22 (Suppl. 1):S63 (2007).
International Preliminary Report on Patentability and Written Opinion for Intl. Pat. Appln. No. PCT/US2011/049776, dated Apr. 16, 2013, 6 pp.

* cited by examiner

*Primary Examiner* — David Lukton
(74) *Attorney, Agent, or Firm* — Foley & Lardner LLP

(57) ABSTRACT

The disclosure provides methods of treating X-linked hypophosphatemia, related bone demineralization and renal phosphate wasting disorders in a mammalian subject. The methods comprise administering to the subject an effective amount of a polyarginine peptide.

20 Claims, 15 Drawing Sheets

D6R Effects on Bone Fgf23 mRNA

Effects of D6R on Bone Growth in Normal and *Hyp*-Mice

Normal    *Hyp*      Normal      *Hyp*
Saline Treated      D6R Treated

Micro-CT Images of Bone from Saline and D6R Treated Normal and *Hyp*-Mice

Micro-CT Images of Bone from Saline and D6R Treated Normal and *Hyp*-Mice

**Effects Of D6R Administration On Mineralized Bone Volume In *Normal* And *Hyp* Mice**

**Goldner Stained Sections of Bone From Saline and D6R Treated Normal and *Hyp*-Mice**

Effects Of D6R Administration On Osteoid Surface In *Normal* And *Hyp* Mice

Effects Of D6R Administration On Bone Mineral Apposition Rate In Normal And Hyp Mice

A

B

Effects Of D6R Administration On Bone Mineral Apposition Rate In Normal And Hyp Mice

METHODS FOR THE TREATMENT OF X-LINKED HYPOPHOSPHATEMIA AND RELATED DISORDERS

CROSS-REFERENCE TO RELATED APPLICATIONS

The present application is a continuation-in-part of PCT International Application No. PCT/US2011/049776, filed on Aug. 30, 2011, and claims the benefit of U.S. Provisional Application No. 61/393,132, filed on Oct. 14, 2010, the entire contents of which are herein incorporated by reference in their entirety.

STATEMENT OF FEDERALLY FUNDED RESEARCH

This invention was made with government support under AR027032 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 15, 2011, is named 99944244.txt and is 3,547 bytes in size.

TECHNICAL FIELD

The present technology relates generally to compositions and methods for treating X-linked hypophosphatemia, tumor-induced osteomalacia, related bone mineralization diseases, and other renal phosphate wasting disorders. In particular embodiments, the present technology relates to administering polyarginine peptides in effective amounts to prevent or treat X-linked hypophosphatemia, tumor-induced osteomalacia and related bone disorders in mammalian subjects.

BACKGROUND

The following description is provided to assist the understanding of the reader. None of the information provided or references cited is admitted to be prior art to the present invention.

Hypophosphatemic rickets presents with rickets and osteomalacia in growing children and associated bone abnormalities, such as bowing of the lower extremities, and osteomalacia in adults. Most cases of X-linked hypophosphatemic rickets, which shows a prevalence of about 1:20,000 live births, are associated with X-linked dominant loss-of-function mutations in the gene PHEX or in the case of autosomal dominant hypophosphatemic rickets, an autosomal dominant gain-of-function mutations in the gene FGF23. X-linked hypophosphatemia (XLH) is characterized by a renal tubular abnormality resulting in phosphate wasting and consequent hypophosphatemia. XLH is the prototypic renal phosphate wasting disorder, characterized in general by progressively severe skeletal abnormalities and growth retardation. The hyp-mouse model harbors a homologous mutation and is an excellent mimic of the human disease. Indeed, much of our understanding of the pathophysiology of XLH derives from studies of the murine homologue.

In contrast, tumor-induced osteomalacia (TIO) is a sporadic condition characterized by remission of the bone disease after resection of a coexisting tumor. The tumors have been of mesenchymal origin in the large majority of patients. However, the observation of TIO concurrent with breast carcinoma, prostate carcinoma, oat cell carcinoma, small cell carcinoma, multiple myeloma, and chronic lymphoctytic leukemia indicates that the disease is likely secondary to a variety of tumors, including those of epidermal and endodermal derivation. Both XLH and TIO have an elevated serum FGF23 level and associated abnormal proximal renal tubular function, resulting in hypophosphatemia, as well as rickets and osteomalacia and the bone abnormalities associated with these mineralization defects. In addition, the disorders are characterized by low or inappropriately normal serum 1,25-dihydroxyvitamin D [1,25(OH)$_2$D] levels.

The gene that is associated with XLH is PHEX (phosphate-regulating gene with homologies to endopeptidases on the X-chromosome), which encodes a 749 amino acid type I membrane protein. Various mutations in the PHEX gene, which are believed to impair the function of the PHEX protein, have been identified in XLH patients; however, the molecular mechanism by which a functional loss of this gene product leads to hypophosphatemic rickets is still uncertain.

The clinical expression of XLH is widely variable, ranging from a mild abnormality, the apparent isolated occurrence of hypophosphatemia, to severe rickets and/or osteomalacia. In children, the most common clinically evident manifestations include short stature and limb deformities associated with rickets. The majority of children with the disease exhibit enlargement of the wrists and/or knees secondary to rickets, as well as bowing of the lower extremities and short stature. Additional signs of the disease may include late dentition, tooth abscesses secondary to poor mineralization of the interglobular dentine, and premature cranial synostosis. Many of these features do not become apparent until the age of 6 to 12 months or older. In spite of marked variability in the clinical presentation, bone biopsies in affected children and adults invariably reveal low turnover osteomalacia without osteopenia. The severity of the bone disorder has no apparent relationship to gender, the extent of the biochemical abnormalities, or the severity of the clinical disability. In untreated youths and adults, the serum 25(OH)D levels are normal and the concentration of 1,25(OH)$_2$D is in the low to normal range. The paradoxical occurrence of hypophosphatemia and normal serum calcitriol levels is due to aberrant regulation of renal 25(OH)D-1α-hydroxylase activity. Studies in hyp- and gy-mice, the murine homologues of the human disease, have established that defective regulation is confined to the enzyme localized in the proximal convoluted tubule, the site of abnormal phosphate transport.

Patients with TIO usually present with bone and muscle pain, muscle weakness, and, occasionally, recurrent fractures of long bones. Additional symptoms common to younger patients are fatigue, gait disturbances, slow growth, and skeletal abnormalities, including bowing of the lower extremities. The duration of symptoms before diagnosis ranges from 2.5 months to 19 years. The age at diagnosis is generally the sixth decade, with a range of 7 to 74 years. Approximately 20% of the patients are younger than 20 years at presentation. The biochemical abnormalities of the disorder include hypophosphatemia and an abnormally low renal tubular maximum for the reabsorption of phosphorus per liter of glomerular filtrate (TmP/GFR), indicative of renal phosphate wasting. The serum phosphorus values range from 0.7 to 2.4 mg/dL. Additional abnormalities include gastrointestinal malabsorption of phosphorus, which, coupled with renal phosphorus wasting, results in a negative phosphorus balance. Serum 25(OH)D is normal and serum 1,25(OH)$_2$D inappropriately normal relative to the hypophosphatemia. Aminoaciduria, most frequently glycinuria, and glucosuria are occasionally present. Radiographic abnormalities include generalized osteopenia, pseudofractures, and coarsened trabeculae, as well as widened epiphyseal plates in children and bone biopsy evidence of osteomalacia in children and adults.

SUMMARY

The present technology relates generally to the treatment of X-linked hypophosphatemia, TIO, bone demineralization and degradation, and other renal phosphate wasting disorders in mammals through administration of therapeutically effective amounts of polyarginine peptides to subjects in need thereof.

In one aspect, the present disclosure describes a method for treating XLH, TIO, hypophosphatemic rickets, and/or osteomalacia in a mammalian subject in need thereof, the method comprising administering to the subject a therapeutically effective amount of a polyarginine peptide. In some embodiments, the hypophosphatemic osteomalacia is tumor-induced osteomalacia. The disclosure also includes a method for enhancing or normalizing bone growth or bone mineralization in a subject suffering from hypophosphatemic rickets, osteomalacia, or other disorders, comprising administering to the subject a therapeutically effective amount of a polyarginine peptide. In some embodiments, administering the polyarginine peptide increases bone mineralization in the subject compared to a control, e.g., a diseased control, subject not administered the polyarginine peptide.

The present disclosure also describes a method for increasing or normalizing the activity of SPC2 in bone cells of a hypophosphatemic subject in need thereof, comprising administering to the hypophosphatemic subject a therapeutically effective amount of a polyarginine peptide, wherein the bone SPC2 activity is increased in the hypophosphatemic subject compared to a control, e.g., a diseased control, subject not administered the polyarginine peptide. In some embodiments, the polyarginine peptide increases the expression of 7B2 mRNA in the subject compared to a control subject not administered the polyarginine peptide. In some embodiments, the polyarginine peptide increases the activity of the 7B2•SPC2 protein complex in the subject compared to a control subject not administered the polyarginine peptide. In some embodiments, FGF23 and SOST mRNA expression are decreased in the subject compared to a control subject not administered the polyarginine peptide. In some embodiments, Npt2a mRNA expression is increased or normalized in the subject compared to a control subject not administered the polyarginine peptide. In some embodiments, administering the polyarginine peptide normalizes or increases degradation of serum FGF23 in the subject compared to a control subject not administered the polyarginine peptide.

In some embodiments, administering the polyarginine peptide increases serum phosphate in the subject compared to a control, e.g., a diseased control, subject not administered the polyarginine peptide. In some embodiments, the polyarginine peptide comprises from 5 to 16, 5 to 12, or 6 to 11 arginine residues (SEQ ID NO: 9). In some embodiments, the polyarginine peptide comprises L-arginine residues or D-arginine residues. In some embodiments, the polyarginine peptide is selected from the group consisting of: penta-L-arginine (SEQ ID NO: 1), hexa-L-arginine (SEQ ID NO: 2), hepta-L-arginine (SEQ ID NO: 3), octa-L-arginine (SEQ ID NO: 4), or nona-L-arginine (SEQ ID NO: 5). In some embodiments, the polyarginine peptide is penta-D-arginine, hexa-D-arginine, hepta-D-arginine, octa-D-arginine, or nona-D-arginine.

In some embodiments, the polyarginine peptide lacks an N-terminal acetyl group, or wherein the polyarginine peptide lacks a C-terminal amide group, or wherein the polyarginine peptide lacks both an N-terminal acetyl group and a C-terminal amide group.

In some embodiments, the polyarginine peptide is fused to a targeting agent. In some embodiments, the targeting agent is a bone targeting agent. In some embodiments, the bone targeting agent is selected from the group consisting of a bisphosphonate, a hydroxybisphosphonate, a phosphonate, a phosphate, an aminomethylenephosphonic acid, and an acidic peptide. In some embodiments, the bone targeting agent is covalently linked to the polyarginine peptide via a linker that is cleaved under physiological conditions. In some embodiments, the linker is an acid-cleavable linker. In some embodiments, the linker is an enol ether, ketal, imine, oxime, hydrazone, semicarbazone, acylimide, or methylene radical. In some embodiments, the linker is a hydrolytically cleavable linker. In some embodiments, the linker is cleaved enzymatically.

In some embodiments, the polyarginine peptide is administered orally, topically, intranasally, intraperitoneally, intravenously, or subcutaneously. In some embodiments, the polyarginine peptide is administered by injecting the peptide into the lumen of a bone. In some embodiments, the subject is a human.

In one aspect, the present disclosure provides a method for treating renal failure in a mammalian subject in need thereof, comprising administering to the subject a therapeutically effective amount of a polyarginine peptide. Elevated FGF-23 is an independent risk factor for end-stage renal disease in patients with relatively preserved kidney function and for mortality across the spectrum of chronic kidney disease. In some embodiments, administering the polyarginine peptide normalizes or decreases FGF23 in the subject compared to a control subject, e.g., a diseased control, not administered the polyarginine peptide. Such therapy in patients with early renal compromise, therefore, may provide unprecedented delay in the progression to end stage renal disease. Moreover, limiting the elevation of FGF23 in early or end state renal disease may lessen mortality due to compromised renal function.

DETAILED DESCRIPTION

Figure 1:
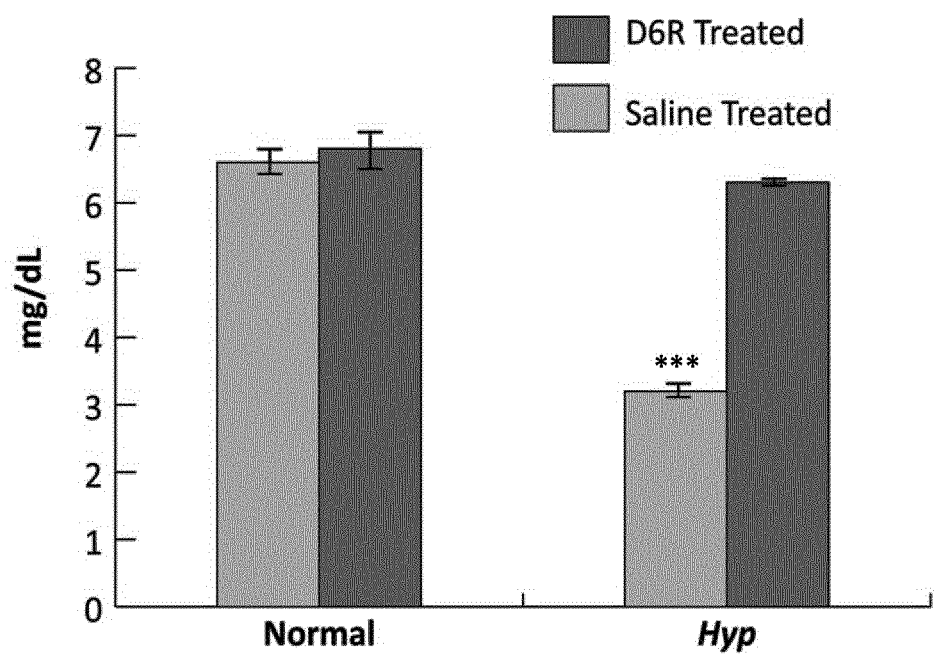
FIG. 1 is a graph showing the effects of hexa-D-arginine (D6R) on serum phosphorus in normal and hyp mice. ***Significantly different from saline and D6 treated Normal and D6R treated Hyp at $p<0.001$.

It is to be appreciated that certain aspects, modes, embodiments, variations and features of the invention are described below in various levels of detail in order to provide a substantial understanding of the present invention.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a peptide" includes a combination of two or more peptides, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "bone mineralization" refers broadly to the processes of bone formation, calcification and homeostasis. Thus, bone mineralization includes the formation of solid bone structures that occurs during growth, development, bone remodeling and wound healing and also to the normal maintenance of differentiated bone structures.

As used herein, the term "effective amount" refers to a quantity sufficient to achieve a desired therapeutic and/or prophylactic effect, e.g., an amount which results in the prevention of, or a decrease in, hypophosphatemic rickets and/or osteomalacia. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In the methods described herein, polyarginine peptides may be administered to a subject having one or more signs or symptoms of XLH, such as hypophosphatemia, rickets and/or osteomalacia. For example, a "therapeutically effective amount" of the polyarginine peptides is meant levels in which the physiological effects of a hypophosphatemic rickets and/or osteomalacia are, at a minimum, ameliorated.

As used herein, the terms "normalize", "normalization", "normalizes", or "normalizing" refers to levels, amounts, ratios or concentrations of a biomolecule or rate of a biomolecular process (e.g., rates or levels of mRNA, protein, protein cleavage or degradation, serum phosphate levels, bone mineralization, bone growth, etc.), which are maintained, increased, decreased and/or returned to control levels (e.g., from a healthy subject) or homeostatic levels after treatment, e.g., treatment with a polyarginine peptide.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may include amino acid sequences modified either by natural processes, such as post-translational processing, or by chemical modification techniques that are well known in the art.

As used herein, the term "subject" refers to a mammal, such as a human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like. Typically, subjects are, or are suspected to be, afflicted with, for example, X-linked hypophosphatemia, tumor-induced osteomalacia, related bone mineralization diseases, and/or other renal phosphate wasting disorders. The term "control subject", as used herein, refers to a subject or population of subjects that do not receive administration of a therapeutically effective amount of a peptide, e.g., a polyarginine peptide such as, for example, D6R.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for XLH or other renal phosphate wasting disorders if, after receiving a therapeutic amount of the polyarginine peptides according to the methods described herein, the subject shows observable and/or measurable reduction in or absence of one or more signs and symptoms of the disorder, such as, e.g., hypophosphatemia, rickets and/or osteomalacia and short stature. It is also to be appreciated that the various modes of treatment or prevention of medical conditions as described are intended to mean "substantial", which includes total but also less than total treatment or prevention, and wherein some biologically or medically relevant result is achieved.

As used herein, the term "tumor-induced osteomalacia" or "TIO" refers to a tumor-acquired syndrome characterized mainly by hypophosphatemia, hyperphosphaturia, abnormally low serum level of 1,25-dihydroxyvitamin D, and osteomalacia. Tumors associated with TIO are mainly of mesenchymal origin such as hemangiopericytomas, although carcinoma of prostate and lung, fibrous dysplasia of bone, linear sebaceous nevus syndrome, neurofibromatosis, and oat cell carcinoma are also associated with TIO. These tumors secrete a phosphatonin, e.g., FGF-23.

As used herein, the term "X-linked hypophosphatemia" ("XLH"), also called X-linked dominant hypophosphatemic rickets, X-linked vitamin D-resistant rickets or hypophosphatemic vitamin D-resistant rickets (HPDR), is an X-linked dominant form of rickets (or osteomalacia) that differs from most cases of rickets in that ingestion of vitamin D is relatively ineffective. Symptoms of XLH include bone deformity, resulting in short stature and genu varum (bow leggedness). XLH is associated with a mutation in the PHEX gene (Xp.22) and subsequent inactivity of the PHEX protein.

Methods of Treating X-Linked Hypophosphatemia and Related Conditions

The present technology relates to the treatment of XLH, TIO, related bone demineralization, and other renal phosphate wasting disorders by administration of polyarginine peptides. In therapeutic applications, compositions or medicaments are administered to a subject suspected of, or already suffering from a disease in an amount sufficient to cure, or at least partially arrest, the symptoms of the disease, including its complications and intermediate pathological phenotypes in development of the disease. As such, the invention provides methods of treating an individual afflicted with XLH, bone demineralization, osteomalacia and/or other renal phosphate wasting disorders, such as tumor-induced osteomalacia (TIO).

Figure 3A:
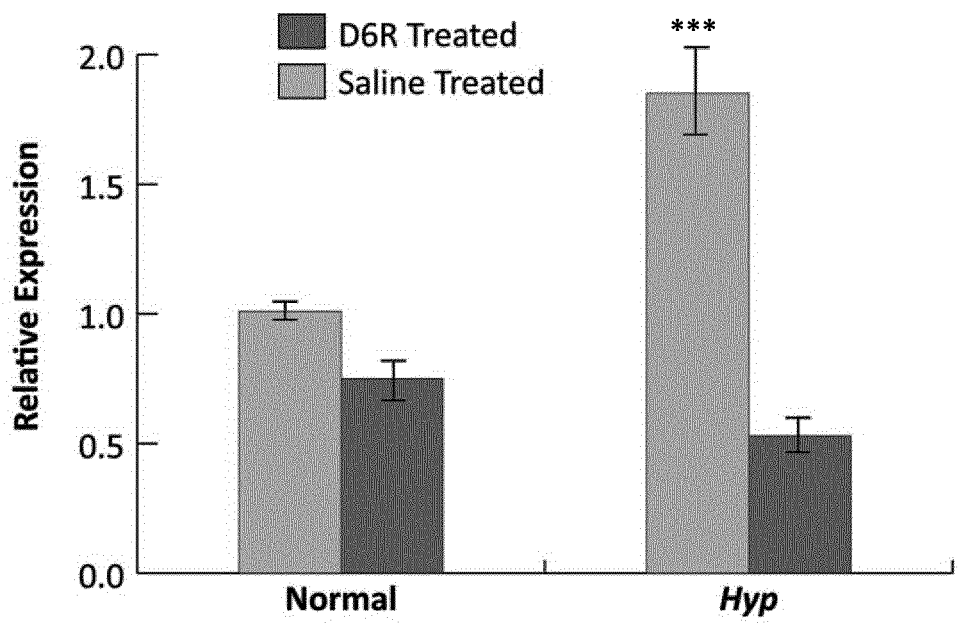
FIG. 3A is a graph showing the effects of D6R on Fgf23 mRNA expression in normal and hyp mice. ***Significantly different from saline and D6 treated Normal and D6R treated Hyp at $p<0.001$.
Figure 3B:
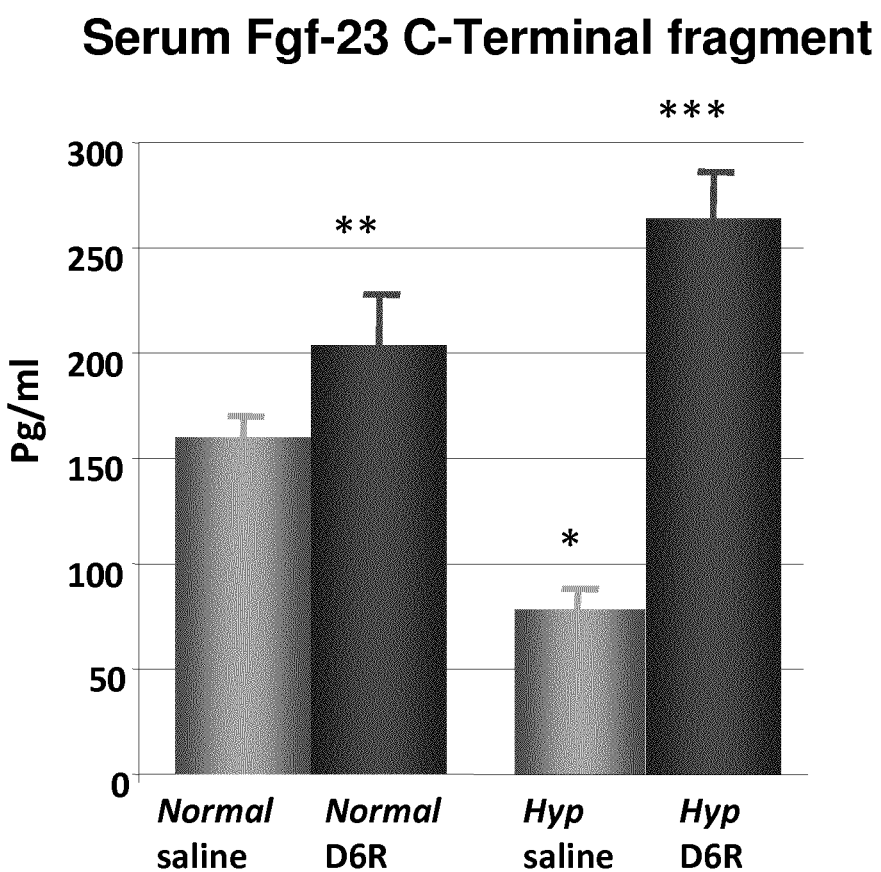
FIG. 3B is a graph showing the effects of D6R on Fgf23 protein cleavage of the C-terminal fragment in normal and hyp mice. *$p<0.01$ when compared to corresponding Normal; $p<0.05$ when compared to corresponding controls; *$p<0.001$ when compared to corresponding controls.

The present inventors discovered that increased serum FGF-23 levels in hyp-mice, a mammalian model of XLH, results from impaired degradation and enhanced production of FGF23. See FIGS. 3A and 3B. Decreased PHEX-dependent 7B2 production in osteoblasts, and diminished 7B2•SPC2 (subtilisin-like protein convertase 2) protein complex activity, underlie the increased serum FGF23 and biochemical phenotype in the hyp-mouse. The present inventors discovered that XLH, related bone demineralization, and/or other renal phosphate wasting disorders can be treated by administering a poly arginine peptide, e.g., hexa-D-arginine (D6R) peptide, which increases 7B2•SPC2 activity and normalizes the biochemical and bone phenotype of XLH in the mutant mice. See FIGS. 5-10.

Figure 4:
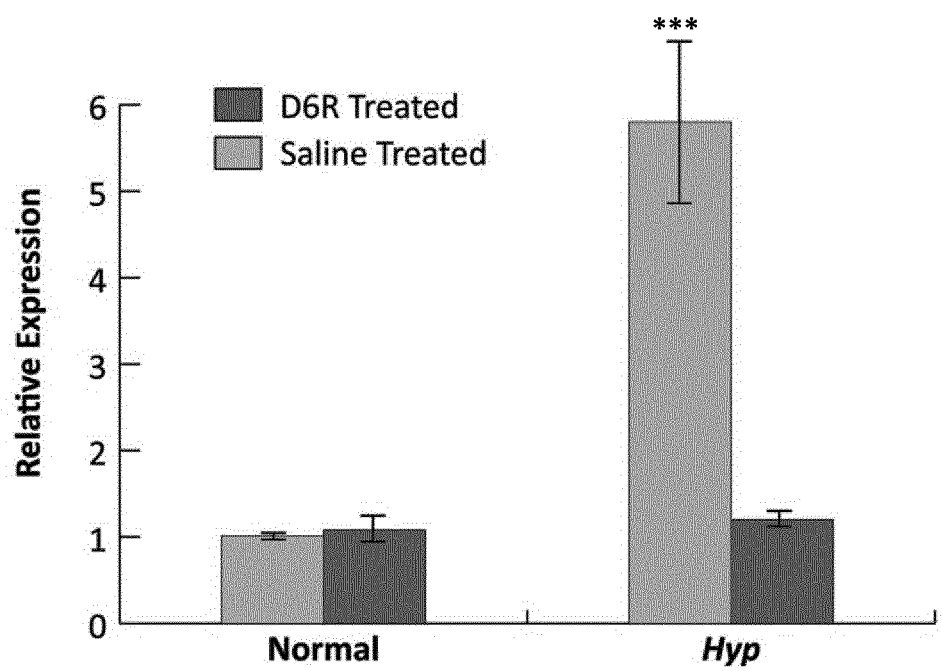
FIG. 4 is a graph showing the effects of D6R on SOST mRNA expression in normal and hyp mice. ***Significantly different from saline and D6 treated Normal and D6R treated Hyp at p<0.001.
Figure 5:
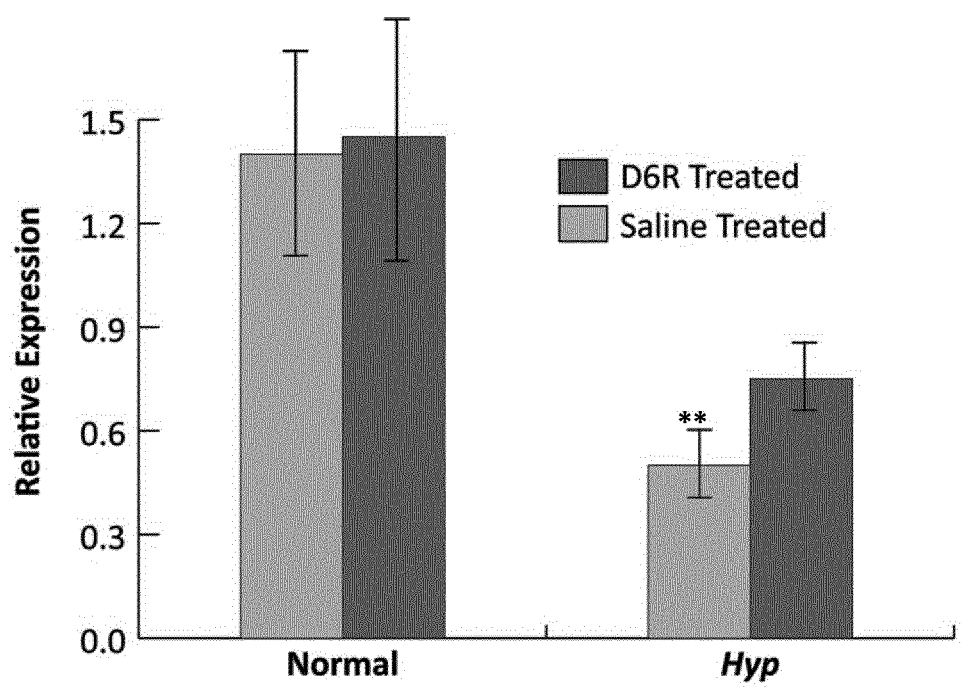
FIG. 5 is a graph showing the effects of D6R on bone 7B2 mRNA expression in normal and hyp mice. ***Significantly different from saline at p<0.01 and D6 treated Hyp at p<0.05.
Figure 6:
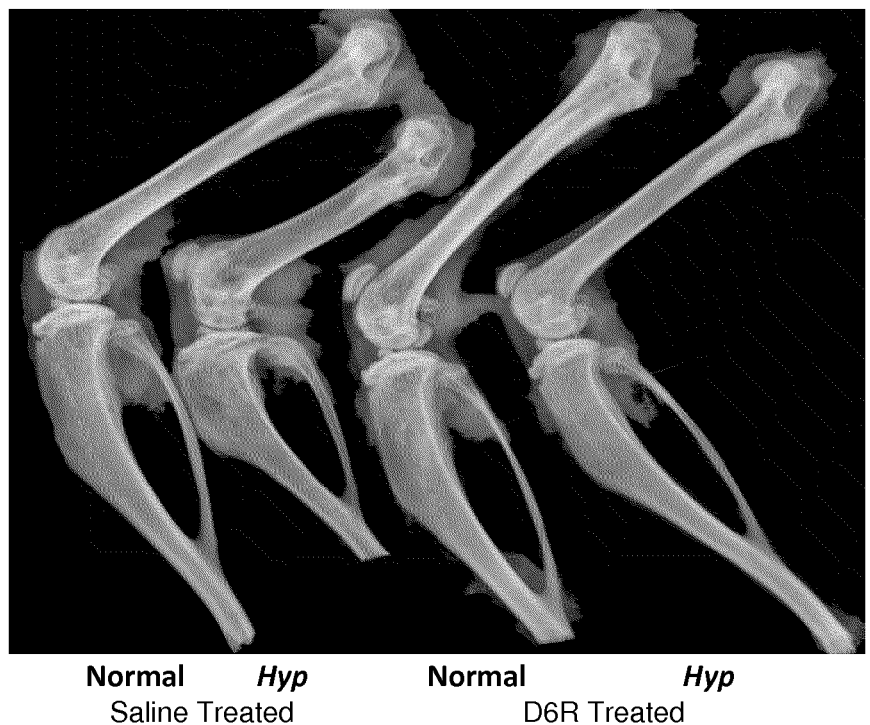
FIG. 6 is a series of X-ray images showing the effects of D6R on bone growth in normal and hyp mice.
Figure 7:
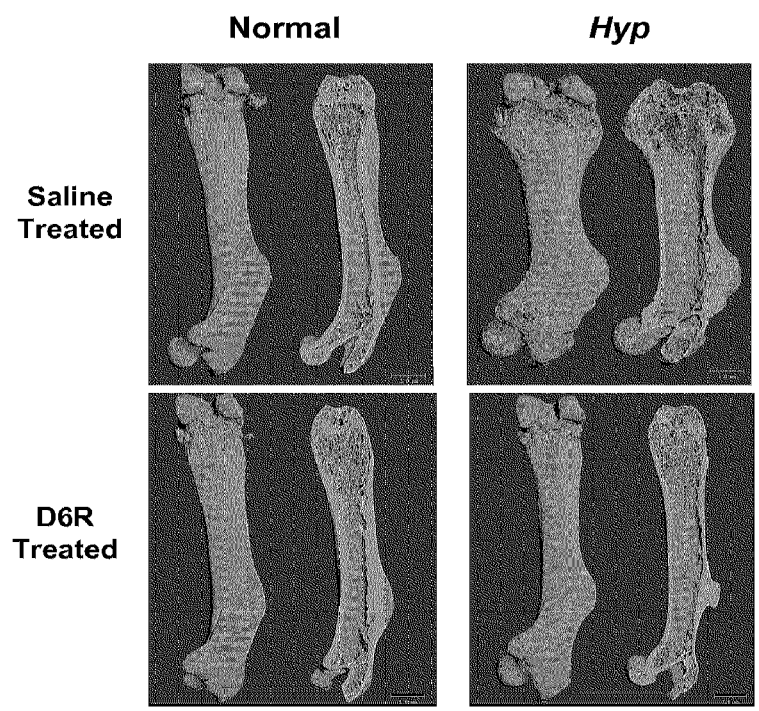
FIG. 7 is a series of micro-CT images showing the effects of D6R on bones in normal and hyp mice.
Figure 8:
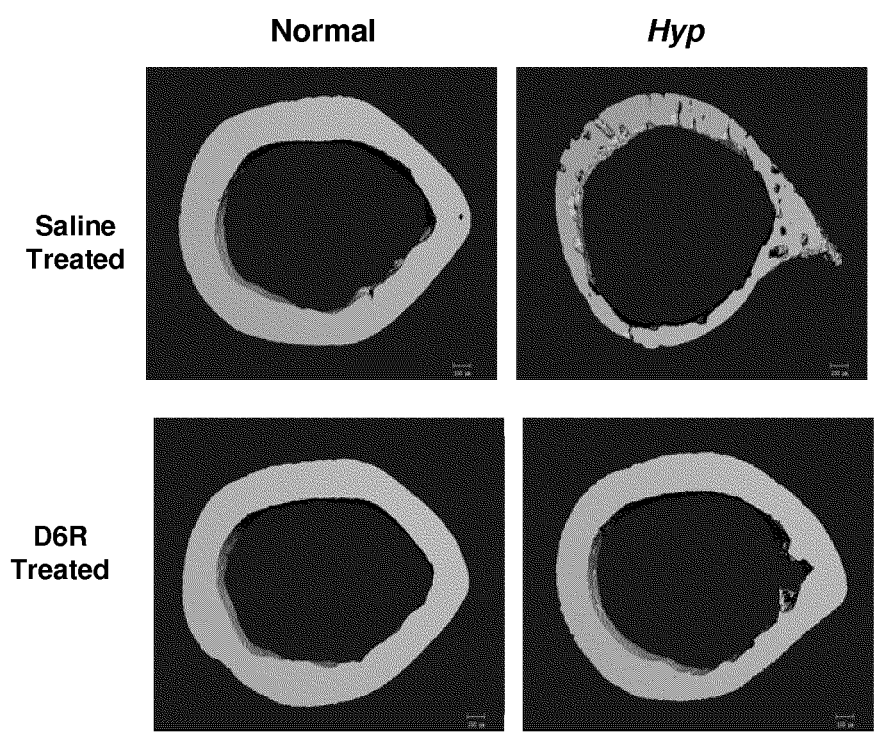
FIG. 8 is a series of micro-CT images showing the effects of D6R on bones in normal and hyp mice.
Figure 9:
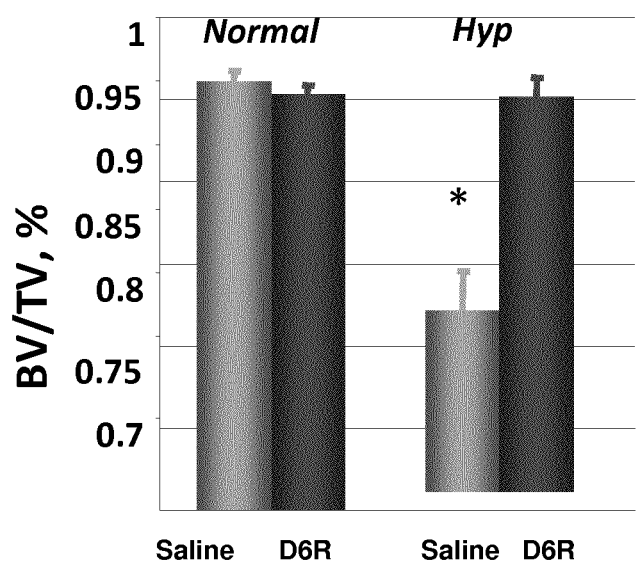
FIG. 9 is a graph showing the effects of D6R administration on mineralized bone density (volume) in normal and hyp mice. *Significantly different from saline and D6 treated Normal and D6R treated Hyp at p<0.01.

Arginine peptides, e.g., D6R, facilitate the degradation of FGF23 to its carboxy- and amino-terminal fragments and reduces the expression of both FGF23 mRNA and SOST mRNA (see FIGS. 3-4), which in turn improves bone mineralization and heals bone diseases, such as, but not limited to, rickets and osteomalacia. Likewise, increased cleavage of proBMP1 and DMP1, as well as increased Npt2a mRNA and protein levels, are factors which can mediate serum phosphate levels, FGF23 and SOST mRNA. Such factors serve as downstream indicators of peptide, e.g., D6R, efficacy via increased 7B2•SPC2 activity.

Accordingly, the present technology encompasses methods of treating hypophosphatemia-related diseases, such as XLH, tumor-induced osteomalacia and other related bone disorders. Surprisingly, the instant methods also result in enhanced bone growth in mammalian subjects. See FIG. 6. Without wishing to be limited by theory, the normalization of bone mineralization is due not only to normalized FGF23 level, but also to normalized Sclerostin level. Such positive effects of arginine peptides, e.g., D6R, are mediated by increasing 7B2•SPC2 activity, as described herein.

Polyarginine peptides and their derivatives can be used, either alone or in conjunction with other active agents, in a pharmaceutical composition for the therapeutic treatments described herein. In some embodiments, a pharmaceutical composition comprising a polyarginine peptide is administered to a subject in an effective amount to treat hypophosphatemia-related diseases, or to ameliorate the symptoms associated therewith. In suitable embodiments, the pharmaceutical composition is capable of restoring normal serum phosphate levels and/or bone mineralization in the subject.

The pharmaceutical compositions identified herein as effective for their intended purpose can be administered to subjects or individuals susceptible to or at risk of developing diseases associated with abnormal phosphate transport at the kidney. When the agent is administered to a subject such as a mouse, a rat or a human patient, the agent can be added to a pharmaceutically acceptable carrier and systemically or topically administered to the subject. Therapeutic amounts can be empirically determined and will vary with the pathology being treated, the subject being treated and the efficacy and toxicity of the agent.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

In various embodiments, suitable in vitro or in vivo assays are performed to determine the effect of a specific polyarginine peptide-based therapeutic and whether its administration is indicated for treatment. In various embodiments, assays can be performed with representative animal models, such as the hyp mouse, to determine if a given polyarginine peptide-based therapeutic exerts the desired effect in treating XLH and related disorders. Compounds for use in therapy can be tested in other suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

Polyarginine Peptides

The compounds used in the present methods include polyarginine peptides or analogues or derivatives thereof. As used herein, the term "polyarginine peptide" includes any of the polyarginine peptides known in the art. The polyarginine peptide can comprise up to about 40, 30, 25, 20, 15, 12, 10, 9, 8, 7, or 6 arginine residues (SEQ ID NO: 10). For example, the peptide can include about 5-40, about 5-30, about 5-25, about 5-20, about 5-15, about 5-10, about 6-20, about 6-15, or about 6-12 arginine residues. In suitable embodiments, the peptide comprises 25 or fewer, 20 or fewer, 15 or fewer or 12 or fewer arginine residues.

Suitable peptides include peptides having an amino acid sequence which includes multiple contiguous arginine residues, and typically, at least three, four, five, six, seven or more contiguous arginine residues. Specific examples of peptides which can be used in the methods of the invention include peptides having the sequences RRRRR (SEQ ID NO: 1); RRRRRR (SEQ ID NO: 2); RRRRRRR (SEQ ID NO: 3); RRRRRRRR (SEQ ID NO: 4); RRRRRRRRR (SEQ ID NO: 5); RRRRRRRRRR (SEQ ID NO: 6); RRRRRRRRRRR (SEQ ID NO: 7); RRRRRRRRRRRR (SEQ ID NO: 8).

In some embodiments, the polyarginine compounds are L-peptides, that is, each of the chiral amino acid residues within the peptide has an L-configuration. In another embodiment, the peptides also include one or more amino acid residues in the D-configuration. In yet another embodiment, the peptides include amino acid residues in which all of the amino acid residues are in the D-configuration. The peptides can also include other non-natural amino acid residues, including non-natural amino acid residues having basic or cationic side chains, for example, side chains which include primary, secondary, tertiary or quaternary amino groups, imino groups or guanidino groups. Systematic substitution of one or more amino acids of an amino acid sequence with a D-amino acid of the same type (e.g., D-arginine in place of L-arginine) may be used to generate more stable peptides.

The polyarginine compounds can optionally include modifying groups attached to the C-terminus, the N-terminus or both. For example, suitable modifying groups which can be attached to the C-terminus include substituted and unsubstituted amino groups, for example, —$NH_2$, —NH(alkyl) and —N(alkyl)$_2$ groups; and alkoxy groups, such as linear, branched or cyclic $C_1$-$C_6$-alkoxy groups. A suitable C-terminal modifying group is the —$NH_2$ group. Additional modifying groups which can be attached to the N-terminus include acyl groups, such as the acetyl group; and alkyl groups, suitably $C_1$-$C_6$-alkyl groups, such as methyl. Further suitable modifying groups that may be attached to the polyarginine compounds include additional amino acid residues, e.g., up to 4, 3, 2 or 1 amino acid residues. The additional amino acid residues may be attached to the C-terminus, the N-terminus or both.

The polyarginine peptides are intended to include peptides comprised of naturally-occurring amino acids, as well as peptide derivatives, peptide analogues and peptide mimetics of the naturally-occurring amino acid structures. The terms "peptide analogue", "peptide derivative" and "peptidomimetic" as used herein are intended to include molecules which mimic the chemical structure of a peptide and retain the functional properties of the peptide. Approaches to designing peptide analogues, derivatives and mimetics are known in the art. For example, see Farmer, P. S. in *Drug Design* (E. J. Ariens, ed.) Academic Press, New York, 1980, vol. 10, pp. 119-143; Ball. J. B. and Alewood, P. F. (1990) *J. Mol. Recognition.* 3:55; Morgan, B. A. and Gainor, J. A. (1989) *Ann. Rep. Med. Chem.* 24:243; and Freidinger, R. M. (1989) *Trends Pharmacol. Sci.* 10:270.

As used herein, a "derivative" of a peptide or amino acid refers to a form of the peptide or amino acid in which one or more reaction groups on the compound have been derivatized with a modifying (derivative) group. Examples of peptide derivatives include peptides in which an amino acid side chain, the peptide backbone, or the amino- or carboxy-terminus has been derivatized (e.g., peptidic compounds with methylated amide linkages).

An "analogue" of a reference amino acid, as the term is used herein, is an α- or β-amino acid having a side chain which is (a) the same as the side chain of the reference amino acid (when the analogue is a β-amino acid residue, a peptoid, or the D-amino acid enantiomer of the reference acid); (b) is an isomer of the side chain of the reference amino acid; (c) is a homologue of the side chain of the reference amino acid; (d) results from replacement of a methylene group in the side chain of the reference amino acid with a heteroatom or group selected from NH, O and S; (e) results from a simple substitution on the side chain of the reference amino acid or any of the preceding (a) to (c); and/or (f) results from a conservative substitution (discussed infra). Analogues of a reference amino acid further include the reference amino acid or any of (a)-(e) above in which the .alpha.-nitrogen atom is substituted by a lower alkyl group, such as a methyl group. A "homologue" of the given amino acid is an α- or β-amino acid having a side chain which differs from the side chain of the given amino acid by the addition or deletion of from 1 to 4 methylene groups. A simple substitution of an amino acid side chain results from the substitution of a hydrogen atom in the side chain of the given amino acid with a small substituent, such as a lower alkyl group, such as a methyl group; a halogen atom, such as a fluorine, chlorine, bromine or iodine atom, or hydroxy.

Peptide mimetics that are structurally similar to therapeutically useful peptides may be used to produce an equivalent therapeutic or prophylactic effect. The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide backbone modifications (i.e., amide bond mimetics) well known to those skilled in the art. Generally, peptidomimetics are structurally similar to a paradigm peptide (i.e., a peptide that has a biological or pharmacological activity), but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods known in the art. A typical non-peptide linkage is —$CH_2NH$—.

Other examples of isosteres include peptides substituted with one or more benzodiazepine molecules (see, e.g., James, G. L. et al. (1993) *Science* 260:1937-1942). Other possible modifications include an N-alkyl (or aryl) substitution, backbone crosslinking to construct lactams and other cyclic structures, substitution of all D-amino acids for all L-amino acids within the compound. Other derivatives include C-terminal hydroxymethyl derivatives, 0-modified derivatives (e.g., C-terminal hydroxymethyl benzyl ether) and N-terminally modified derivatives including substituted amides such as alkylamides and hydrazides. Such peptide mimetics may have advantages over other peptides, including, for example: more economical production, greater chemical stability, enhanced pharmacological properties (e.g., half-life, absorption, potency, efficacy, and the like), altered specificity (e.g., a broad-spectrum of biological activities), reduced antigenicity, and others. Derivitization of peptidomimetics should not substantially interfere with the desired biological or pharmacological activity of the peptidomimetic.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc, New York (1997).

Bone Targeting Agents

In some embodiments, the polyarginine peptide may be linked to a bone targeting agent via a linker that is cleaved under physiological conditions. As used herein, the term "bone targeting agent" refers to a ligand (e.g., a chemical moiety antibody, or peptide) that reversibly binds to bone tissue and is suitably not toxic to a mammal, especially a human. For instance, the bone targeting agent can be a ligand that binds hydroxyapatite, a major component of bone and dental structures. Polyarginine peptide can be targeted to calcium deposits in regions of the body other than bone, such as calcium deposits in the arteries, heart, kidney, or gall bladder. However, the bone targeting agent ideally selectively binds to bone tissue. In other words, the bone targeting agent suitably binds to bone tissue with at least 2-fold greater affinity (e.g., at least 3-fold, at least 5-fold, at least 10-fold, or at least 25-fold greater affinity) than the bone targeting agent binds to non-bone tissue.

In suitable embodiments, the bone targeting agent reversibly binds to bone tissue, meaning that the bone targeting agent is eventually released from bone and expelled from the body. The bone targeting agent remains bound to bone tissue for a sufficient period of time to allow cleavage of the linker and release of a desired dose of polyarginine peptide to target cells. The bone targeting agent can remain bound to bone for about 10 minutes (e.g., about 20 minutes, about 30 minutes, about 1 hour, or about 3 hours) to about 6 months (e.g., about 90 days, about 120 days, or about 150 days) after cleavage of the linker, after which the bone targeting agent is expelled from the body. The bone targeting agent can remain bound to bone for about 6 hours (e.g., about 12 hours, about 24 hours, about 48 hours, about 3 days, about 7 days, or about 14 days) to about 60 days (e.g., about 30 days or about 45 days) post-cleavage of the linker. Candidate bone targeting agents can be screened in vitro by determining affinity to bone tissue (e.g., hydroxyapatite) in, for example, a multi-well format. Candidate bone targeting agents also can be screened in vivo by assessing the rate and timing of excretion of candidate bone targeting agents from the body. In this respect, the bone targeting agent suitably is expelled from the body via the kidneys.

The bone targeting agent may be selected from the group consisting of a bisphosphonate, a hydroxybisphosphonate, a phosphonate, a phosphate, an aminomethylenephosphonic acid, and an acidic peptide. Polyphosphonic acids and aminomethylenephosphonic acids have a high affinity for bone in vivo due to their binding of the exposed calcium ions in hydroxyapatite (calcium phosphate), and also are suitable for use in the context of the present methods. The terms "phosphonate, phosphate, and aminomethylenephosphonate" are meant to encompass the phosphonic acids, the phosphoric acids, and aminomethylenephosphonic acids, respectively, as well as any salts, hydrolyzable esters, and prodrugs of the phosphorous-based acids thereof. At the biological pH of 7.4 in the blood, or the more acidic pH around the bone, a certain portion of the phosphate or phosphonate of the bone targeting agent may be deprotonated and replaced with a counterion. Furthermore, the exchange of proton for calcium is an inherent event for the binding of the bone targeting agent to the hydroxyapatite in the invention. However, preparation and administration of the composition containing the bone targeting agent may or may not require complete protonation of the phosphorous acids therein. Therefore, the phosphonic acid, phosphoric acid, and aminomethylenephosphonic acid are drawn and utilized interchangeably with phosphate, phosphonate, and aminomethylenephosphonate. Biologically hydrolyzable esters of the phosphorus-based acids may also be utilized in the method of the invention. Similarly, prodrugs of the phosphorous-based acids may also be utilized in vivo to mask the acidity of the composition during, for example, formulation and administration.

Other examples of bone targeting agents include, but are not limited to, amino- and hydroxy-alkyl phosphonic and diphosphonic acids; hydroxybisphosphonic acids including alendronate, pamidronate, 4-aminobutylphosphonic acid, 1-hydroxyethane-1,1-diphosphonic acid, and aminomethylenebisphosphonic acid; phosphates such as phytic acid; and aminomethylenephosphonic acids such as N,N-bis(methylphosphono)-4-amino-b-enzoic acid and nitrilotri(methylphosphonic acid). It is envisioned that these bone targeting agents can be attached through one of the heteroatoms or by chemical modification that installs an additional attachment point.

DOTMP and EDTMP (ethylene diamine-N,N,N',N'-tetrakis(methylenephosp-honic acid) are other examples of bone seeking agents. Derivatization of these compounds can be performed by a variety of chemical processes, such as the coupling chemistry and alkylation chemistry. The coupling chemistry is further described in Vieira de Almedia et al., *Tetrahedron*, 55, 12997-13010 (1999). Alkylation chemistry involving DOTMP has been further described in Chavez et al., *Biomedical Imaging: Reporters, Dyes, & Instrumentation*, Contag & Sevick-Muracia, Eds., Proc. SPIE, Vol. 3600, 99-106 (July, 1999). Alkylation chemistry for other phosphonic acids is further described in, for example, U.S. Pat. No. 5,177,064, U.S. Pat. No. 5,955,453, de Lombaert et al., *J Med Chem.*, 37, 498-511 (1994), and Iyer et al., *Tetrahedron Letters*, 30(51), 7141-7144 (1989). EDTMP can be connected to the linker by one of the phosphorous oxygens to create a phosphonate linkage. Alternatively, EDTMP can be chemically modified to generate ABDTMP by installation of an aniline group. The aniline amine is then available to form, for example, an amide bond with a linker and attach to the cell protection factor.

In some embodiments, the polyarginine peptide is covalently attached to the bone targeting agent via a linker that is cleavable under physiological conditions. Upon administration to a mammal, the polyarginine peptide-bone targeting agent conjugate attaches to bone tissue (or another calcium-containing structure), the linkage between the moieties is cleaved, and the polyarginine peptide is released in active form to act on cells in the surrounding area. The conjugate comprising the polyarginine peptide covalently linked to a bone targeting agent can, therefore, be considered a "prodrug," which is activated upon cleavage of the linker and release of the active polyarginine peptide.

In some embodiments, the linker comprises an organic moiety comprising a nucleophilic or electrophilic reacting group which allows covalent attachment to the bone targeting agent. In some embodiments, the linker is an enol ether, ketal, imine, oxime, hydrazone, semicarbazone, acylimide, or methylene radical. The selection of a particular linker will depend on the target environment and the desired release kinetics of the cell protection factor from the bone targeting agent. Desirably, the linker is an acid-cleavable linker, a hydrolytically cleavable linker, or enzymatically-cleavable linker. By "acid-cleavable" is meant that the linkage between the cell protection factor and bone targeting agent is cleaved below pH 7. For example, an acid cleavable linker, such as ACL-3, can link a bone targeting agent and a polyarginine peptide. In linking a peptide moiety (e.g., polyarginine peptide) to a bone targeting agent, the anhydride group of an acid-cleavable linker, such as ACL-3, reacts first with the free amino group of the peptide. In a subsequent step, the isothiocyanato is reacted with the amino groups of the bone-seeking moiety at higher pH to create a stable thiourea linkage. Under acidic conditions, the peptide-ACL-3 amide linkage is readily cleaved, freeing the native amino group of the protein. Osteoclastic bone resorption involves an acidic-mediated mechanism. At any given time, it is estimated that 15-20% of the bone surface is involved in resorption, formation, or mineralization. The pH at the bone surface during the osteoclastic bone resorption process has been measured using microelectrodes to be as low as pH 4.7 (Ghosh et al., *J. Chem. Soc. Perkin Trans.* 1, 8, 1964 (1979)). It has been demonstrated that small molecules (and ions such as calcium) liberated from the bone surface via osteoclasts are transported through the osteoclast to the extracellular space and can diffuse into nearby tissues, such as the bone marrow (see, for example, Stepensky et al., "Bone as an Effect Compartment: Models for Uptake and Release of Drugs" in *Clinical Pharmacokinetics,* 42(10), 863-881 (2003)).

Modes of Administration and Effective Dosages

Any method known to those in the art for contacting a cell, organ or tissue with a peptide may be employed. In vivo methods typically include the administration of an peptide, such as those described above, to a mammal, suitably a human. When used in vivo for therapy, the peptides are administered to the subject in effective amounts (i.e., amounts that have desired therapeutic effect). The dose and dosage regimen will depend upon the degree of the disease in the subject, the characteristics of the particular peptide used, e.g., its therapeutic index, the subject, and the subject's history.

The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be desirable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The oral compositions, in some embodiments, include peptide stabilizing agents which prevent, decrease, and/or lessen the likelihood of peptide degradation, e.g., a polyarginine peptide. Non-limiting examples of such agents include starch-g-poly(acrylic acid) copolymers, starch/poly(acrylic acid) mixtures, endopeptidase inhibitors, trypsin inhibitors, chymotrypsin, aprotinin inhibitors, pepsin inhibitors, carboxypeptidase inhibitors, elastase inhibitors, exopeptidase inhibitors, aminopeptidase inhibitors, carboxypeptidase inhibitors, chelating agents, polyethylene glycol (PEG), amphiphilic oligomers and/or polymers, carboxymethyl starch (CMS) excipients containing protease inhibitors, etc. See, e.g., Ameye et al., "Trypsin inhibition, calcium and zinc ion binding of starch-g-poly(acrylic acid) copolymers and starch/poly(acrylic acid) mixtures for peroral peptide drug delivery." *Journal of Controlled Release*. Vol. 75(3), pp. 357-364 (2001); Bernkop-Schnurch et al., "Multifunctional matrices for oral peptide delivery." *Crit Rev Ther Drug Carrier Systems*. Vol. 18(5):459-501 (2001).

Furthermore, peptide degradation of polyarginine peptides, for example, can be inhibited or decreased in some embodiments via enzyme masking strategies, peptide conjugation, adding cleavable linkers, etc., and the like. See, e.g.,
Witt, K., and Davis, T., "CNS Drug Delivery: Opioid Peptides and the Blood-Brain Barrier." *The AAPS Journal*, Vol. 8(1), pp. 76-88 (2006). For example, peptide modifications including, but not limited to, amino terminal modifications (e.g., N-acylation or pyroglutamyl residue additions), carboxy terminal modifications, glycosylation, polymer conjugation, vector-based conjugation, nutrient-coupled transport, prodrug derivatization with cleavable linkers, and cyclization of peptides can increase peptide stability and half-life and/or decrease peptidase activity thereby decreasing concomitant peptide degradation of, for example, a poly arginine peptide. Other modes for reducing peptide degradation of, e.g., a polyarginine peptide, and/or increasing peptide stability of the same include, for example, the introduction of conformational constraints, altering chirality, steric modifications, and/or the use of one or more non-natural amino acid residues. See McLean, D. "Modifications of Peptide Compositions to Increase Stability and Delivery Efficiency." U.S. Patent Publication No. 2009/0042769.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In some embodiments, transdermal administration may be performed my iontophoresis.

A therapeutic peptide can be formulated in a carrier system. The carrier can be a colloidal system. The colloidal system can be a liposome, a phospholipid bilayer vehicle. In some embodiments, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In some embodiments, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In some embodiments, the polymer is poly-lactic acid (PLA) or copoly lactic/glycolic acid (PGLA).

The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)). Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3):201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100:63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices may be desirable. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies suitably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the peptides, sufficient for achieving a therapeutic or prophylactic effect, range from about 0.000001 mg per kilogram body weight per day to about 10,000 mg per kilogram body weight per day, per week, per month, or per year. Suitably, the dosage ranges are from about 0.0001 mg per kilogram body weight per day to about 100 mg per kilogram body weight per day. For example dosages can be 1 mg/kg body weight or 100 mg/kg body weight every day, every two days or every three days or within the range of 1-100 mg/kg every week, every two weeks or every three weeks or within the range of 1-100 mg/kg every month, every two months, every three months, every four months, every five months, or every six months. An exemplary treatment regime entails administration once per day, once a week or once per month. In therapeutic applications, a relatively high dosage at relatively short intervals is sometimes required until progression of the disease is reduced or terminated, and typically until the subject shows partial or complete amelioration of symptoms of disease. Thereafter, the patient can be administered a prophylactic regime. The schedule of doses would be optimized to maintain the therapeutic concentration at the target tissue, most preferably by single daily or weekly administration.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a suitable embodiment, the mammal is a human.

EXAMPLES

The present invention is further illustrated by the following example, which should not be construed as limiting in any way.

In these examples, the effect of a hexa-D-arginine (D6R) peptide in treating XLH in a mouse model was investigated. Patients with XLH and hyp-mice, a murine homologue of the human disease, have a loss of function mutation in the PHEX/Phex gene, which results in an increase of the serum FGF/Fgf-23 concentration, resulting hypophosphatemia, renal phosphate (Pi) wasting, abnormal vitamin D metabolism, bone demineralization and rickets and/or osteomalacia.

Taking an alternative approach to identifying treatment strategies for XLH, we have explored the Phex-dependent downstream effects in osteoblasts that underlie the HYP phenotype. We found that decreased Phex-dependent osteoblast production of 7B2, the co-factor for subtilisin-like protein convertase 2 (SPC2) results in decreased 7B2•SPC2 enzyme activity and underlies elevated serum Fgf-23, the primary biochemical abnormality in the murine homologue of XLH, the Hyp-mouse. In addition, decreased 7B2•SPC2 enzyme activity also enhances production of bone Sost mRNA and increases the concentration of the encoded protein, Sclerostin. Thus, the abnormal enzyme activity increases both Fgf23 and Sclerostin, the known potential causes of abnormal bone mineralization in XLH. In this study, we show that treatment of Hyp-mice with hexa-D-arginine (D6R) increases 7B2•SPC2 activity and normalizes the biochemical and bone phenotypes in the mutant mice.

Experimental Design

In Vivo Injection of D6R in Normal and Hyp Mice:

3-week old normal and hyp mice were randomly separated into two groups for each strain. One group of mice received daily ip injection of saline. The other group of mice received daily ip injection of D6R 1.5 μg/kg/day for 5 weeks. Blood samples were obtained every 3 days via retro-orbital bleedings. At the end of the in vivo injection period, the animals were euthanized with an overdose of sodium pentobarbital (65 mg/kg). The final blood sample was collected by cardiac puncture for large volume of serum preparation. Kidney and femoral bone samples were collected for total RNA and protein extractions.

Biochemistry Measurements:

Serum Pi levels were measured using Phosphorus Liqui-UV kit from Stanbio Laboratory (Boerne, Tex.). Serum Ca levels were measured using calcium Liquicolor kit from Stanbio following the manufacturer's protocols. Serum intact FGF-23 was measured employing a FGF-23 ELISA kit obtained from Kainos Laboratories, Japan. Serum C-terminal FGF-23 was measured using ELISA kit from Immunotopics, CA.

Real-Time RT-PCR for mRNA Expression:

Total RNA was isolated from kidney samples and femurs. The femurs were trimmed of all fat, homogenized into fine powder in liquid nitrogen using porcelain motor and pestle. Total RNA was then extracted using TRIzol Reagent (Invitrogen, CA) following the manufacturer's protocol. Kidney samples were rinsed free of blood using ice-cold PBS buffer. Then the kidney was homogenized in TRIzol Reagent using mortor and pestle. Then, the renal total RNA was isolated following the manufacturer's protocol. RT reactions were performed using Bio-Rad iScript cDNA synthesis kit (Bio-Rad, CA) with poly-A primers. FGF-23 mRNA, as well as Npt2 mRNA and $25(OH)D_3$-1α-hydroxylase mRNA were quantitated by real-time PCR using gene specific primers.

Western Blot for Protein Expression:

Kidney proteins were isolated using sucrose buffer containing 20 mM HEPES, 1 mM EDTA, 255 mM sucrose, 0.4 mM phenylmethylsulfonyl fluoride, and 2 μg/ml leupeptin. The homogenate was centrifuged at 1,500 g for 15 min, and the pellet containing mitochondrial protein, including $25(OH)D$-1α-hydroxylase, was re-suspended in the same buffer, aliquoted, and stored at −80° C. until use. The supernatant that contained the plasma membrane protein obtained after centrifugation was also collected for the measurement of Npt2 protein. Bone samples were homogenized into fine powder in liquid nitrogen. Protein contents were isolated using T-PER tissue protein extraction reagent with Halt protease inhibitor cocktail (Thermo Scientific, Rockford, Ill.).

A 20 μg aliquot of the respective protein extracts was electrophoresed in 10% SDS-PAGE gel and transferred onto a nitrocellulose membrane. The membrane was then washed and probed with specific antibodies and subsequently with specific secondary antibodies conjugated with HRP. To quantitate the immunoblotting signal, 6 ml of chemiluminescence detection solution (ECL plus, Amersham, UK) was added, and the signal was detected directly by the fluorescent scanner (Storm 860, Amersham, UK). Band density was analyzed using ImageQuant 5.2 software (Molecular Dynamics, Sunnyvale, Calif.). The antibody was then removed by incubating the membrane in reprobing solution (62.5 mM Tris-HCl, 2% SDS, and 100 mM 2-mercaptoethanol, pH 6.7) for 30 min, 50° C. The membrane was then blocked and probed with specific anti-β-actin antibody to verify the loading equivalence among samples.

High-Resolution Radiography (x-Ray) for the Femus:

mouse femurs were extracted and incubated in lysis buffer (2×SSC, 0.2% SDS, 10 mM EDTA, 10 mg/ml proteinase K) for 2 days. After the surrounding muscles were digested, the femurs were washed in PBS buffer and X-rayed on a Faxitron model MX-20 Specimen Radiography System with a digital camera attached (Faxitron x-ray Corp., Buffalo Grove, Ill.).

Double Fluorochrome Labeling of the Long Bone:

To analyze the changes in bone formation (mineralization) rate, double fluorescence labeling was performed as follows: a calcein label (5 mg/kg i.p.; Sigma-Aldrich, St. Louis, Mo.) was administered to the mice 8 days prior the end of the experiment. This was followed by injection of an Alizarin Red label (20 mg/kg i.p.; Sigma-Aldrich) 5 days later. Mice were sacrificed 48 h after injection of the second label, and the femurs were removed and fixed in 2% paraformaldehyde and 2.5% glutaraldehyde at room temperature for 4 h before serial dehydration.

The specimens were then dehydrated through a graded series of ethanol treatments (70-100%) and embedded in MMA without prior decalcification. 100 μm sections were cut using a Leitz 1600 saw microtome. The unstained sections were viewed under epifluorescent illumination using a Nikon E800 microscope, interfaced with the Osteomeasure histomorphometry software (version 4.1, Atlanta, Ga.) to calculate the osteoid ratios determined by the mean distance between the two fluorescent labels divided by the number of days between labels (μm/day).

Resin Casted Scanning Electron Microscopy (SEM):

Femur bone was dissected, fixed in 2% paraformaldehyde and 2.5% glutaraldehyde in 0.1 M cacodylate buffer solution (pH 7.4) at room temperature for 4 h and then transferred to 0.1 M cacodylate buffer solution. The specimens were dehydrated in ascending concentrations of ethanol, embedded in methyl-methacrylate (MMA, Buehler, Lake Bluff, Ill.) and then surface polished using 1 μm and 0.3 μm alumina alpha micropolish II solution (Buehler) in a soft cloth rotating wheel. The surface was acid etched with 37% phosphoric acid for 10 s, followed by 5% sodium hypochlorite for 5 min. The samples were then coated with gold and palladium and examined using an FEI/Philips XL30 Field emission environmental scanning electron microscope (Hillsboro, Oreg.).

Results

Figure 2A:
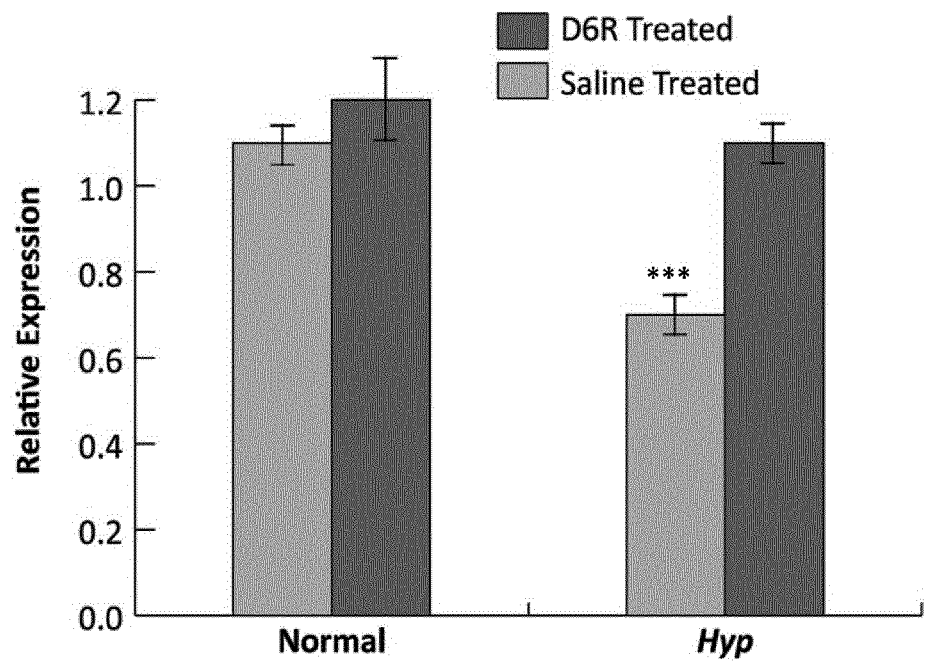
FIG. 2A is a graph showing the effects of D6R on Npt2a mRNA expression in normal and hyp mice. *Significantly different from saline and D6 treated Normal and D6R treated Hyp at $p<0.001$.
Figure 2B:
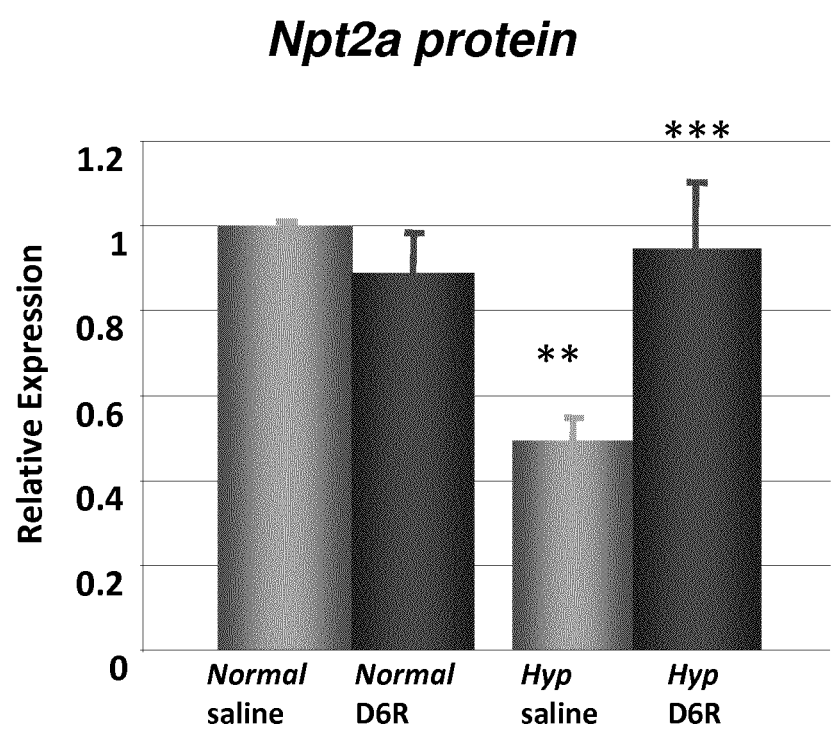
FIG. 2B is a graph showing the effects of D6R on Npt2a protein levels in normal and hyp mice. $p<0.01$ from corresponding Normal; ***$p<0.01$ from corresponding saline treated Hyp.

In the hyp mouse model of XLH, treatment with D6R (1.5 μmole/kg/day, ip×5 weeks) decreased Fgf23 mRNA expression (see FIG. 3A) and enhanced degradation of intact FGF23 in hyp-mouse bone. Furthermore, as shown in Table 1 below, D6R administration decreased serum FGF23 concentrations in hyp-mice compare to controls. Moreover, degradation of serum FGF23 was also increased with D6R treatment (see FIG. 3B). Such modification of FGF23 levels, expression, and degradation, in turn, resulted in normalization of Npt2a mRNA (see FIGS. 2A-B) and, in accord, renal phosphate wasting and serum phosphorus levels (see FIG. 1), the cardinal biochemical abnormalities in XLH. Moreover, in response to increased Npt2a production, the unique translational abnormality in renal $25(OH)D_3$-1α-hydroxylase activity was normalized.

TABLE 1

D6R affects serum FGF23 concentration

|  | Normal Mice | Hyp-Mice |
|---|---|---|
| Saline Treated | 200 ± 15.5 | 2126 ± 281 |
| D6R Treated | 120 ± 12.5* | 1682 ± 191* |

*p < 0.001

Figure 10:
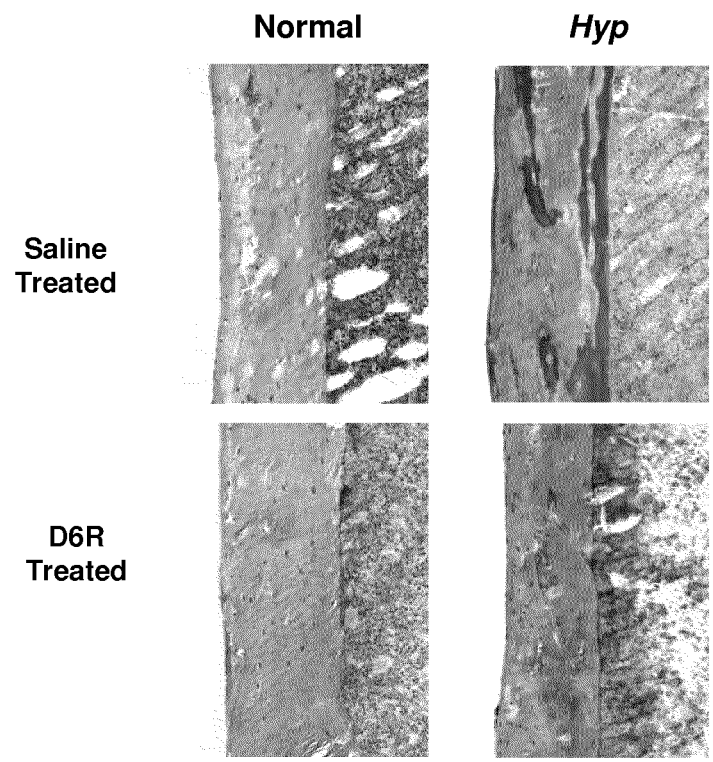
FIG. 10 is a series of Goldner-stained sections of bone showing the effects of D6R in normal and hyp mice.
Figure 11:
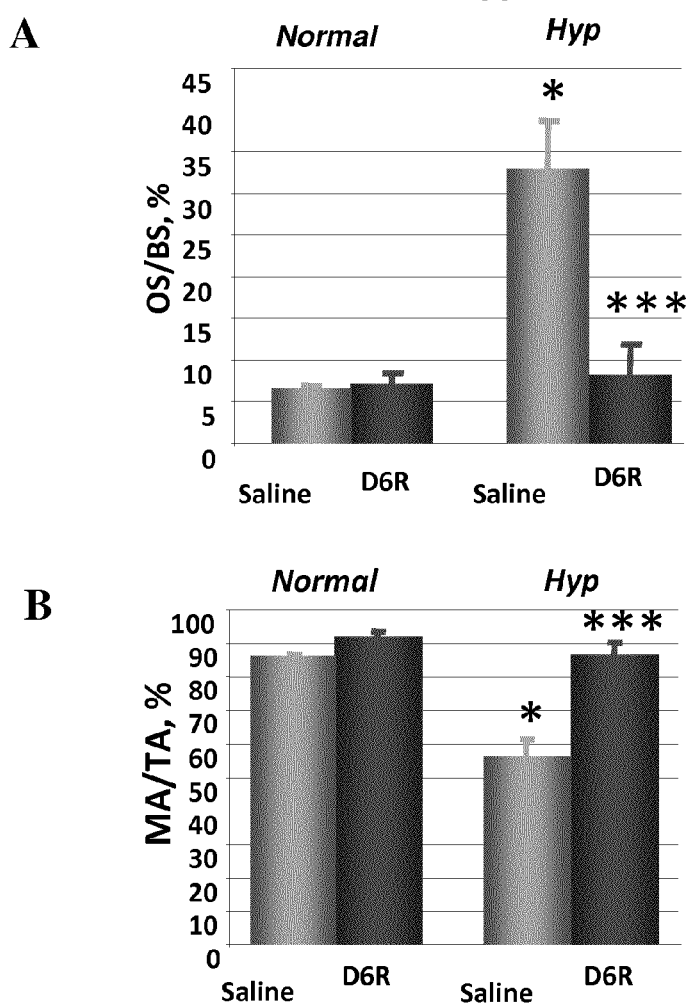
FIG. 11A is a graph showing the effects of D6R administration on osteoid surface in normal and hyp mice (OS/BS %).
FIG. 11B is a graph showing the effects of D6R administration on osteoid surface in normal and hyp mice (MA/TA %). *p<0.01 when compared to corresponding controls; ***p<0.01 when compared to Saline treated Hyp mice.
Figure 12:
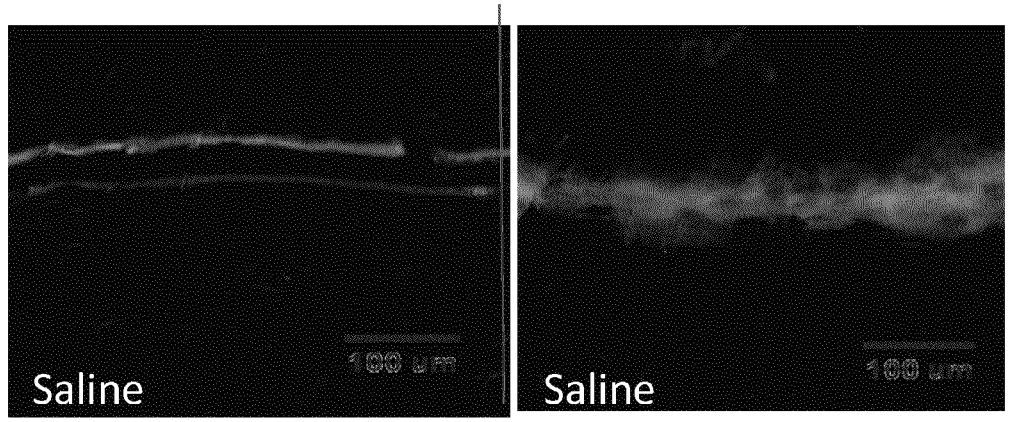
FIG. 12A is a double fluorochrome labeled fluorescent stained section of bone showing the apposition of bone from normal and hyp-mouse bone treated with saline. The hyp-mouse bone reveals decreased bone mineral apposition rate.
FIG. 12B is a double fluorochrome labeled fluorescent stained section of bone showing the mineral apposition rate of normal and hyp-mouse bone treated with D6R. The bone from D6R treated hyp-mice reveal restoration of normal bone mineral apposition rate.
Figure 12:
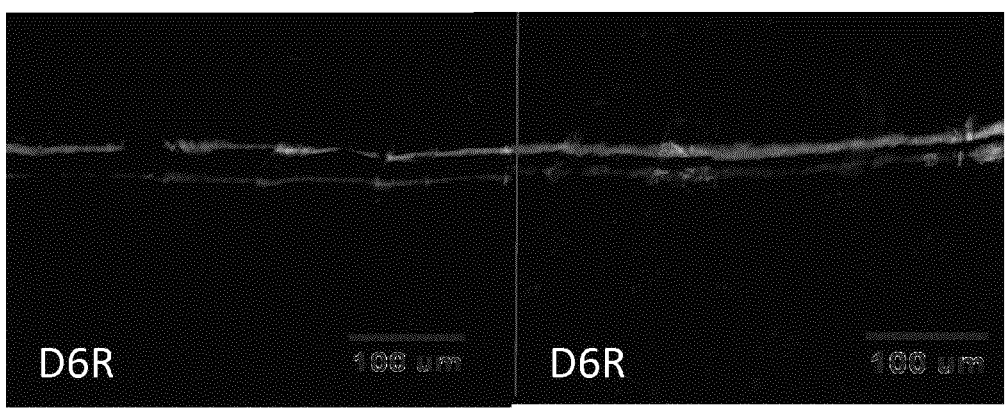
Figure 13:
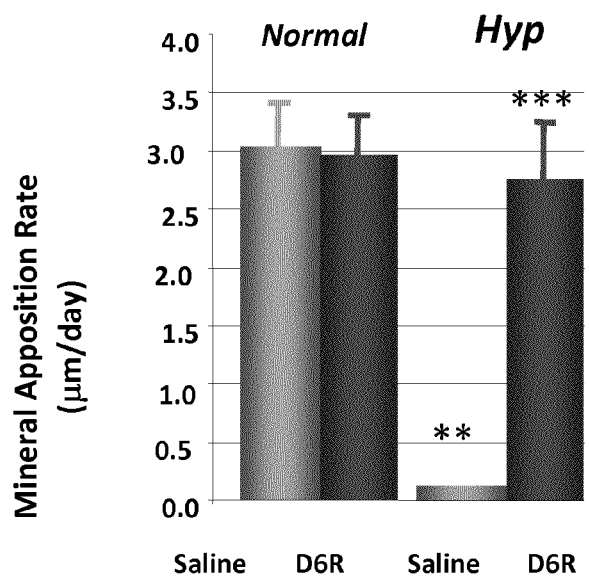
FIG. 13 is a graph showing the effects of D6R on bone mineral apposition rates in normal and hyp mice. p<0.0001 when compared to corresponding controls; *p<0.0001 when compared to corresponding saline treated Hyp mice.

In concert with normalization of these biochemical abnormalities, there is an associated suppression of Sost mRNA and the coded protein Sclerostin. Thus, the treatment r decreases the circulating levels of FGF23 (Table 1) and sclerostin, thereby removing the primary abnormalities underlying the aberrant bone and cartilage mineralization disorders. Specifically, D6R therapy normalized the bone mineralization process, increasing bone density normalization (see FIG. 9), decreasing Osteoid surface/Bone surface (OS/BS) and enhancing the Mineralized area/Total Area (MA/TA ratios). These changes significantly reduced the osteoid surface on the mineralized bone, as seen in FIG. 10, wherein the brown staining excess osteoid in hyp-mouse bone decreases upon treatment. The changes in mineralization upon treatment were quantitated by measurement of the mineral apposition rate, which demonstrated normalization of this process in D6R treated hyp-mice (see FIGS. 12-13). As expected, therefore, our results show that the rickets and osteomalacia, the debilitating and characteristic elements of XLH, are cured upon treatment with D6R (see FIGS. 6-13).

In association with the resultant normalization of mineralization, bone modeling decreased to normal, returning the long bones to normal circumference, and the length on the long bones in the extremities increased, indicative of normal growth, thereby overcoming the short stature, characteristic of the disease. Taken together, these observations indicate that D6R treatment of Hyp-mice corrects the biochemical abnormalities of the disorder, heals the characteristic bone mineralization disorder, and enhances long bone growth, reversing the short stature observed in affected subjects with the disease, thereby identifying a class of drugs that may provide previously unavailable and seemingly minimally toxic treatment for XLH and related disorders.

The dose-dependent effects of D6R (0-200 μM) on SPC2 activity in hTert osteoblasts (MOB) and MC3T3 osteoblasts in culture were also examined. Here, D6R treatment of hTert osteoblasts (50 μM) for 48 hours significantly increased SPC2 activity (121±18 vs 329±17 fluorescent units/min; p<0.01). See Table 2. Treatment of MC3T3 cells for a similar period likewise increased enzyme activity at 200 μM (124±14 vs 171±7 fluorescent units/min; p<0.05). Treatment of the MOB cell line with D6R, and the resulting increase in SPC2 enzyme activity decreased Fgf23 mRNA expression (1.0±0.7 vs 0.2±0.1 fold; p<0.001). It was also revealed that the D6R-dependent enhancement of SPC2 enzyme activity in MOB cells was concomitant with an increase in 7B2 mRNA expression (1.0±0.2 vs 3.6±0.4 fold; p<0.001), but without alteration of SPC2 mRNA expression.

TABLE 2 h-Tert osteoblasts/fluorescent units

| Control | D6R 50 μM |
|---|---|
| 121 ± 18 | 329 ± 17* |

*p < 0.01

Accordingly, the foregoing data illustrate that D6R enhances osteoblast 7B2•SPC2 activity, which normalizes the decreased enzyme function present in the hyp-mouse osteoblast. Moreover, the associated D6R stimulation of 7B2 mRNA expression (see FIG. 5) indicates that increased enzyme activity likely results from enhanced 7B2 production, which overcomes the central Phex-dependent abnormality in the hyp-mouse osteoblast.

Illustrative Embodiments

In an illustrative embodiment, a method for treating hypophosphatemic rickets in a mammalian subject in need thereof is provided, comprising administering to the subject a therapeutically effective amount of a polyarginine peptide. In some embodiments, the hypophosphatemic rickets is due to X-linked hypophosphatemia.

In an illustrative embodiment, a method for treating hypophosphatemic osteomalacia in a mammalian subject in need thereof is provided, comprising administering to the subject a therapeutically effective amount of a polyarginine peptide. In some embodiments, the hypophosphatemic osteomalacia is tumor-induced osteomalacia or is due to X-linked hypophosphatemia.

In an illustrative embodiment, a method for enhancing or normalizing bone growth or bone mineralization in a subject suffering from hypophosphatemic rickets or osteomalacia is provided, comprising administering to the subject a therapeutically effective amount of a polyarginine peptide.

In an illustrative embodiment, a method for increasing or normalizing the activity of SPC2 in a hypophosphatemic subject in need thereof is provided, comprising administering to the hypophosphatemic subject a therapeutically effective amount of a polyarginine peptide, wherein the SPC2 activity is increased in the hypophosphatemic subject compared to a control subject, e.g., a diseased control, not administered the polyarginine peptide.

In some embodiments of the above-described methods, the polyarginine peptide normalizes or increases the expression of 7B2 mRNA in the subject compared to a control subject not administered the polyarginine peptide.

Additionally or alternatively, in some embodiments of the above-described methods, the polyarginine peptide normalizes or increases the activity of the 7B2•SPC2 protein complex in the subject compared to a control subject not administered the polyarginine peptide.

Additionally or alternatively, in some embodiments of the above-described methods, FGF23 and SOST mRNA expression are normalized or decreased in the subject compared to a control subject not administered the polyarginine peptide.

Additionally or alternatively, in some embodiments of the above-described methods, Npt2a mRNA expression or protein levels are increased or normalized in the subject compared to a control subject not administered the polyarginine peptide.

Additionally or alternatively, in some embodiments of the above-described methods, administering the polyarginine peptide normalizes or increases serum phosphate in the subject compared to a control subject not administered the polyarginine peptide.

Additionally or alternatively, in some embodiments of the above-described methods, administering the polyarginine peptide normalizes or increases degradation of serum FGF23 in the subject compared to a control subject not administered the polyarginine peptide.

Additionally or alternatively, in some embodiments of the above-described methods, the polyarginine peptide comprises from 5 to 16 arginine residues (SEQ ID NO: 11).

Additionally or alternatively, in some embodiments of the above-described methods, the polyarginine peptide comprises L-arginine residues or D-arginine residues, or both.

Additionally or alternatively, in some embodiments of the above-described methods, the polyarginine peptide is selected from the group consisting of: penta-L-arginine (SEQ ID NO: 1), hexa-L-arginine (SEQ ID NO: 2), hepta-L-arginine (SEQ ID NO: 3), octa-L-arginine (SEQ ID NO: 4), or nona-L-arginine (SEQ ID NO: 5), or any combination thereof.

Additionally or alternatively, in some embodiments of the above-described methods, the polyarginine peptide is penta-D-arginine, hexa-D-arginine, hepta-D-arginine, octa-D-arginine, or nona-D-arginine, or any combination thereof.

Additionally or alternatively, in some embodiments of the above-described methods, the polyarginine peptide is hexa-L-arginine (SEQ ID NO: 2) or hexa-D-arginine, or both.

Additionally or alternatively, in some embodiments of the above-described methods, the polyarginine peptide lacks an N-terminal acetyl group, or wherein the polyarginine peptide lacks a C-terminal amide group, or wherein the polyarginine peptide lacks both an N-terminal acetyl group and a C-terminal amide group.

Additionally or alternatively, in some embodiments of the above-described methods, the polyarginine peptide is fused to a targeting agent.

Additionally or alternatively, in some embodiments of the above-described methods, the targeting agent is a bone targeting agent selected from the group consisting of bisphosphonate, a hydroxybisphosphonate, a phosphonate, a phosphate, an aminomethylenephosphonic acid, and an acidic peptide.

Additionally or alternatively, in some embodiments of the above-described methods, the bone targeting agent is covalently linked to the polyarginine peptide via a linker that is cleaved under physiological conditions.

Additionally or alternatively, in some embodiments of the above-described methods, the linker is an acid-cleavable linker.

Additionally or alternatively, in some embodiments of the above-described methods, the linker is an enol ether, ketal, imine, oxime, hydrazone, semicarbazone, acylimide, or methylene radical.

Additionally or alternatively, in some embodiments of the above-described methods, the linker is a hydrolytically cleavable linker.

Additionally or alternatively, in some embodiments of the above-described methods, the linker is cleaved enzymatically.

Additionally or alternatively, in some embodiments of the above-described methods, the polyarginine peptide is administered orally, topically, intranasally, intraperitoneally, intravenously, or subcutaneously.

Additionally or alternatively, in some embodiments of the above-described methods, the polyarginine peptide is administered by injecting the peptide into the lumen of a bone.

Additionally or alternatively, in some embodiments of the above-described methods, the subject is a human.

In another illustrative embodiment, a method for treating renal failure in a mammalian subject in need thereof is disclosed herein, comprising administering to the subject a therapeutically effective amount of a polyarginine peptide. Additionally or alternatively, in some embodiments of the method, administering the polyarginine peptide normalizes or decreases serum FGF23 in the subject compared to a control subject, e.g., a diseased control, not administered the polyarginine peptide.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating X-linked hypophosphatemia in a mammalian subject in need thereof, comprising administering to the subject a therapeutically effective amount of a polyarginine peptide comprising at least four consecutive arginine residues.

2. The method of claim 1, wherein the subject is suffering from X-linked hypophosphatemic rickets.

3. The method of claim 1, wherein the subject is suffering from X-linked hypophosphatemic osteomalacia.

4. The method of claim 1, wherein the polyarginine peptide comprises from 5 to 16 consecutive arginine residues.

5. The method of claim 1, wherein the polyarginine peptide is selected from the group consisting of penta-D-arginine, hexa-D-arginine, hepta-D-arginine, octa-D-arginine, or nona-D-arginine, or a combination thereof.

6. The method of claim 1, wherein the polyarginine peptide is hexa-D-arginine.

7. The method of claim 1, wherein the polyarginine peptide is fused to a targeting agent.

8. The method of claim 7, wherein the targeting agent is a bone targeting agent.

9. The method of claim 8, wherein the bone targeting agent is selected from the group consisting of bisphosphonate, a hydroxybisphosphonate, a phosphonate, a phosphate, an aminomethylenephosphonic acid, and an acidic peptide.

10. A method for treating hypophosphatemic osteomalacia in a mammalian subject in need thereof, comprising administering to the subject a therapeutically effective amount of a polyarginine peptide comprising at least four consecutive arginine residues.

11. The method of claim 10, wherein the hypophosphatemic osteomalacia is tumor-induced osteomalacia or is due to X-linked hypophosphatemia.

12. The method of claim 10, wherein the polyarginine peptide comprises from 5 to 16 consecutive arginine residues.

13. The method of claim 10, wherein the polyarginine peptide is selected from the group consisting of penta-D-arginine, hexa-D-arginine, hepta-D-arginine, octa-D-arginine, or nona-D-arginine, or a combination thereof.

14. The method of claim 10, wherein the polyarginine peptide comprises hexa-D-arginine.

15. The method of claim 10, wherein the polyarginine peptide is fused to a targeting agent.

16. The method of claim 15, wherein the targeting agent is a bone targeting agent.

17. The method of claim 16, wherein the bone targeting agent is selected from the group consisting of bisphosphonate, a hydroxybisphosphonate, a phosphonate, a phosphate, an aminomethylenephosphonic acid, and an acidic peptide.

18. A method for enhancing or normalizing bone growth or bone mineralization in a subject suffering from hypophosphatemic rickets or hypophosphatemic osteomalacia, comprising administering to the subject a therapeutically effective amount of a polyarginine peptide comprising at least four consecutive arginine residues.

19. The method of claim 18, wherein the polyarginine peptide comprises hexa-D-arginine.

20. The method of claim 19, wherein the polyarginine peptide is fused to a bone targeting agent.

* * * * *

SEQUENCE LISTING

<160> NUMBER OF SEQ ID NOS: 11

<210> SEQ ID NO 1

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Arg Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Arg Arg Arg Arg Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Arg Arg Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg Arg Arg Arg Arg Arg
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

```
Arg Arg Arg Arg Arg Arg Arg Arg Arg Arg
1               5                   10
```

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Arg Arg Arg Arg Arg Arg Arg Arg Arg Arg Arg
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Arg Arg Arg Arg Arg Arg Arg Arg Arg Arg Arg Arg
1               5                   10
```

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16, 5-12 or 6-11
      residues

<400> SEQUENCE: 9

```
Arg Arg Arg Arg Arg Arg Arg Arg Arg Arg Arg Arg Arg Arg Arg Arg
1               5                   10                  15
```

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(16)
<223> OTHER INFORMATION: This sequence may encompass 40, 30, 25, 20, 15,
      12, 10, 9, 8, 7 or 6 residues

<400> SEQUENCE: 10

```
Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg
                20                  25                  30

Arg Arg Arg Arg Arg Arg Arg Arg
        35                  40
```

<210> SEQ ID NO 11
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 11

Arg Arg Arg Arg Arg Arg Arg Arg Arg Arg Arg Arg Arg Arg Arg Arg
1               5                   10                  15
```